United States Patent
Mishra

(10) Patent No.: US 12,014,606 B2
(45) Date of Patent: Jun. 18, 2024

(54) SYSTEM, METHOD AND COMPUTER-ACCESSIBLE MEDIUM FOR ARTIFICIAL INTELLIGENT MARKET MICROSTRUCTURE

(71) Applicant: New York University, New York, NY (US)

(72) Inventor: Bhubaneswar Mishra, Great Neck, NY (US)

(73) Assignee: NEW YORK UNIVERSITY, New York, NY (US)

( * ) Notice: Subject to any disclaimer, the term of this patent is extended or adjusted under 35 U.S.C. 154(b) by 305 days.

(21) Appl. No.: 17/116,653

(22) Filed: Dec. 9, 2020

(65) Prior Publication Data

US 2022/0180709 A1    Jun. 9, 2022

(51) Int. Cl.
*G07F 17/32* (2006.01)
*G06N 3/04* (2023.01)
*G06N 3/044* (2023.01)
*G06N 3/08* (2023.01)
*G06Q 10/06* (2023.01)
(Continued)

(52) U.S. Cl.
CPC ......... *G07F 17/3295* (2013.01); *G06N 3/044* (2023.01); *G06N 3/08* (2013.01);
(Continued)

(58) Field of Classification Search
CPC .................. G06F 17/3295; G06N 3/0445
See application file for complete search history.

(56) References Cited

U.S. PATENT DOCUMENTS 10,402,726 B1 *  11/2019  Moore ................ G06N 3/00
11,164,107 B1 *  11/2021  Craib .................. G06N 99/00
(Continued)

FOREIGN PATENT DOCUMENTS

| CN | 112699414 | * | 8/2020 | |
| CN | 111832606 | * | 10/2020 | |
| CN | 111832606 | * | 11/2020 | ............. G06F 11/36 |

OTHER PUBLICATIONS

Salman and Liu, in "Overfitting Mechanism and Avoidance in Deep Neural Networks," from ARXIV, in 2019 (Year: 2019).*
(Continued)

*Primary Examiner* — Mike Anderson
*Assistant Examiner* — Brandon M Duck
(74) *Attorney, Agent, or Firm* — HUNTON ANDREWS KURTH LLP

(57) ABSTRACT

An exemplary system, method, and computer-accessible medium for recommending a model(s), can include, for example, receiving a plurality of test models including the model(s), determining if each of the test models has at least one verifier associated therewith, and recommending the model(s) based on the determination. An indication of a stake associated with each of the test models can be received. The stake can be a financial stake or a reputation stake. The financial stake can be a cryptocurrency. At least one of the test models can be analyzed using a machine learning procedure, which can be a convolutional neural network or a recurrent neural network. At least one of the test models can be analyzed using an empirical Bayes procedure. A particular model can be removed if the particular model(s) does not have a verifier(s) associated therewith.

20 Claims, 4 Drawing Sheets

(51) Int. Cl.
   *G06Q 10/0639* (2023.01)
   *G06Q 10/067* (2023.01)
   *G06Q 20/06* (2012.01)
   *G06Q 40/04* (2012.01)
   *G16H 40/20* (2018.01)
   *G16H 50/20* (2018.01)
   *G16H 70/20* (2018.01)
   *G06Q 30/0645* (2023.01)
   *G06Q 40/02* (2023.01)

(52) U.S. Cl.
   CPC ..... *G06Q 10/06395* (2013.01); *G06Q 10/067* (2013.01); *G06Q 20/0655* (2013.01); *G06Q 40/04* (2013.01); *G07F 17/3225* (2013.01); *G07F 17/3276* (2013.01); *G06Q 30/0645* (2013.01); *G06Q 40/02* (2013.01); *G06Q 2220/00* (2013.01)

(56) References Cited

U.S. PATENT DOCUMENTS

2020/0117580 A1* 4/2020 Lekivetz .................. G06F 11/36
2020/0348662 A1* 11/2020 Cella ....................... G06N 20/00

OTHER PUBLICATIONS

J. Goodfellow, "NIPS 2016 tutorial: Generative adversarial networks," CoRR, vol. abs/1701.00160, 2017.

B. Efron, "Bayes, oracle bayes, 5 and empirical bayes," 2017.

G. Gao, B. Mishra, and D. Ramazzotti, "Efficient simulation of financial stress testing scenarios with suppes-bayes causal networks," in International Conference on Computational Science, ICCS 2017, Jun. 12-14, 2017, Zurich, Switzerland, pp. 272-284, 2017.

S. Kleinberg and B. Mishra, "The temporal logic of causal structures," in UAI 2009, Proceedings of the Twenty-Fifth Conference on Uncertainty in Artificial Intelligence, Montreal, QC, Canada, Jun. 18-21, 2009, pp. 303-312, 2009.

S. Kleinberg and B. Mishra, "The temporal logic of token causes," in Principles of Knowledge Representation and Reasoning: Proceedings of the Twelfth International Conference, KR 2010, Toronto, Ontario, Canada, May 9-13, 2010, 2010.

B. Efron and T. Hastie, Computer Age Statistical Inference: Algorithms, Evidence and Data Science. Cambridge University Press, 2016.

J. Goodfellow, Y. Bengio, and A. C. Courville, "Deep Learning. Adaptive computation and machine learning," MIT Press, 2016.

* cited by examiner

SYSTEM, METHOD AND COMPUTER-ACCESSIBLE MEDIUM FOR ARTIFICIAL INTELLIGENT MARKET MICROSTRUCTURE

FIELD OF THE DISCLOSURE

The present disclosure relates generally to artificial intelligence, and more specifically, to exemplary embodiments of an exemplary system, method and computer-accessible medium for artificial intelligent market microstructure.

BACKGROUND INFORMATION

In the 1986 book Minsky's Society of Mind, artificial intelligence ("AI") pioneer Marvin Minsky wrote: "What magical trick makes us intelligent? The trick is that there is no trick. The power of intelligence stems from a vast diversity, not from any single, perfect principle." However, it has remained unclear how and when these artificial agents congregate to form such a society of mind. Nonetheless, it has been argued that should such a society emerge from artificial computational building blocks, it will possess a great power as it would view a mind as a society of agents, as opposed to the consequence of some basic principle or some simple formal system. Different agents can be based on different types of processes with different purposes, ways of representing knowledge, and methods for producing results.

Thus, it may be beneficial to provide an exemplary system, method and computer-accessible medium for artificial intelligent market microstructure.

SUMMARY OF EXEMPLARY EMBODIMENTS

An exemplary system, method, and computer-accessible medium for recommending a model(s), can include, for example, receiving a plurality of test models including the model(s), determining if each of the test models has at least one verifier associated therewith, and recommending the model(s) based on the determination. An indication of a stake associated with each of the test models can be received. The stake can be a financial stake or a reputation stake. The financial stake can be a cryptocurrency. At least one of the test models can be analyzed using a machine learning procedure, which can be a convolutional neural network or a recurrent neural network. At least one of the test models can be analyzed using an empirical Bayes procedure. A particular model can be removed if the particular model(s) does not have a verifier(s) associated therewith.

In some exemplary embodiments of the present disclosure, the verifier(s) can be person(s) testing at least some of the test models. An indication of a stake from the one person associated with the verification of the test models can be received. The stake is a financial stake, which can be cryptocurrency. A further indication can be provided to the person(s) of a further stake based on the person(s)' verification of the test models. The verifier(s) can be configured to rank each of the test models. The test model(s) can be analyzed using a dataset. The dataset(s) can be a financial dataset or a medical dataset. The verifier(s) can include a plurality of verifiers, and each of the verifiers can be compared to each other. A utility can be awarded to at least some of the verifiers based on the comparison.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
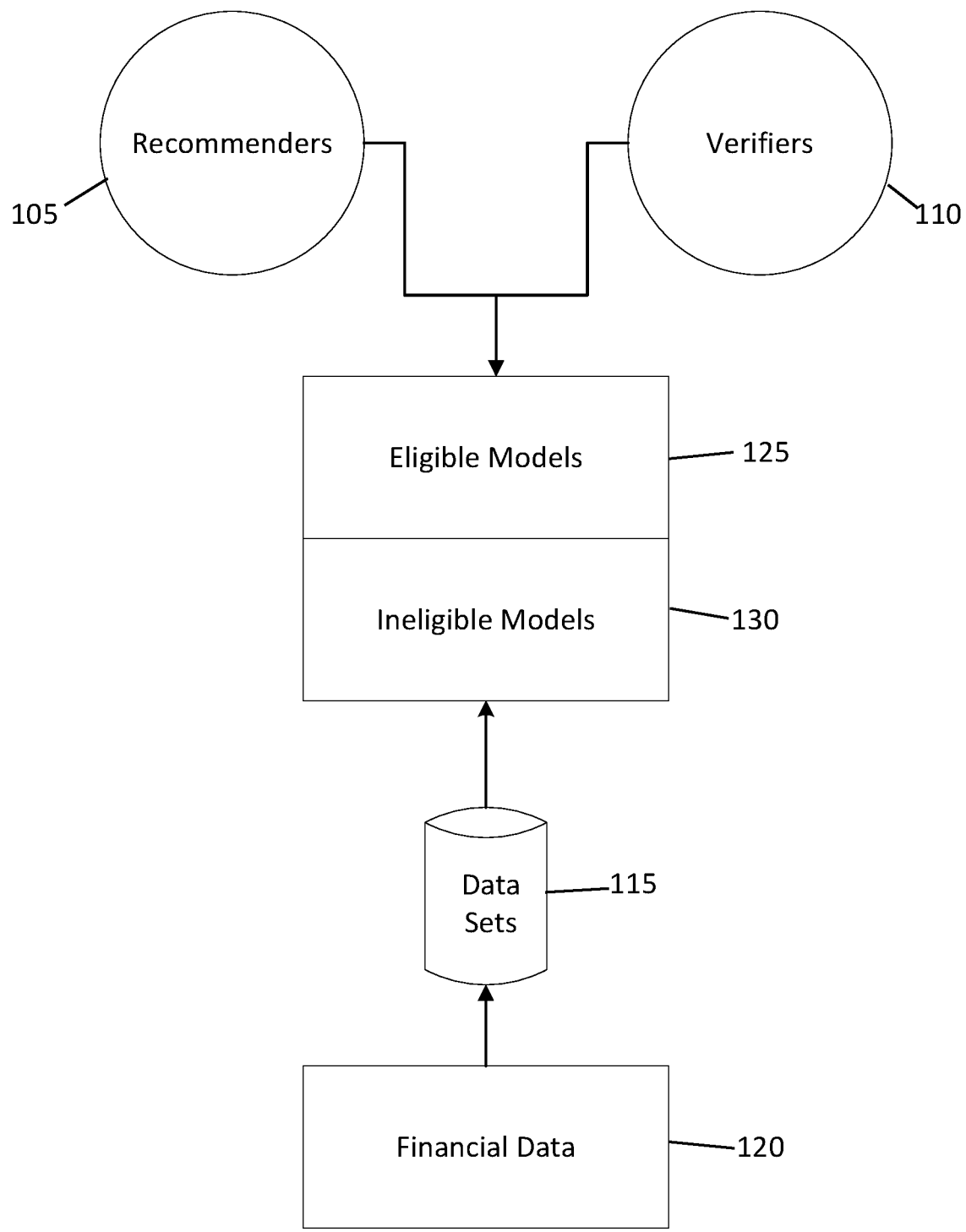
FIG. 1 is an exemplary diagram illustrating market competition according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Classically, intelligence and its role in problem solving have been difficult to formalize. While computability has a widely-accepted model in terms of Church-Turing thesis, Turing-reducibility, and Turing-universality, as a consequence of these, it remains impossible to define its general problem solving capability as there remain interesting decision problems for which their undecidability can be proven; the classical one being the Halting Problem. In fact given two programs: one genuine and other, presumably, imitative, there can be no decision procedure to determine if they are Turing equivalent. These statement have certain implications on how Artificial Intelligence can be defined.

In order to address this, Information-Asymmetric Signaling games can be utilized, which can include certain set of sender agents, some of which can have the type Oracles (e.g., humans) and the others the type Imitators (e.g., models). The senders can send certain signals (e.g., conversational statements in English) to receivers (e.g., humans) who must act by responding to Oracles, but ignoring Imitators. Such a game can be called an Imitation Game and the receiver's test a Turing Test. Similarly, by also assigning types to receivers (e.g., Oracles and Imitators), the Imitation Game can be extended to also include a Reverse Turing test. As a signaling game, the classical Imitation Game and its extension can both have Nash Equilibria: some trivial as Babbling or Pooling but others far more relevant (e.g., separating). Artificial Intelligence can also be defined be in terms of Imitators' ability to achieve a reasonably informative and stable pooling (e.g., non-separating) Nash Equilibrium when introduced into a society of human Oracles. In other words, the receiver must respond in exactly the same manner independent of whether the sender is an Oracle or Imitator.

The exemplary system, method, and computer-accessible medium, according to an exemplary embodiment of the present disclosure, can extend this approach to include additional, non-strategic, agents (e.g., Recommenders and Verifiers). They can have no explicit utilities to optimize, or even, satisfice, other than those described in terms of betting and winning, or losing certain tokens. These tokens can be cryptographic objects, which can be difficult to counterfeit (e.g., replicate or manufacture); transactions among recommenders and verifiers can be verified in terms of various local and global properties (e.g., expressed in terms of a model-checkable logic, for example, propositional temporal logic), assuming that a non-tamperable model (e.g., a Kripke structure) can be dynamically created by some other agents, who can employ costly-signaling. While it can be unspecified as to how the Recommenders and Verifiers and their models can be constructed and deployed, as long as they satisfy certain system-wide distributed liveness (e.g., Recommender's responsibilities) and safety (e.g., Verifier's responsibilities) conditions, the exemplary system, method, and computer-accessible medium can result in, and maintain, a stable Nash equilibrium that can also be pooling (e.g., Imitators can be indistinguishable from Oracles).

The exemplary system, method, and computer-accessible medium, according to an exemplary embodiment of the present disclosure, can be used to facilitate two sets of non-strategic agents (Recommenders and Verifiers), whose interactions can be used to reach and maintain Nash equilibria.

Exemplary AI Architecture

As discussed herein, AI can broadly refer to many diverse approaches that can include, for example, Statistical Inference, Econometrics, Data Science, Big Data, Probably Approximate Computational ("PAC") Learning, Heuristics, Machine Learning, etc., all of which employ large-scale data and scalable computing The exemplary architecture can include:
1. Multiple exemplary AI modules ("Models" M's) in an ensemble, working on multiple data sets ("Domains" D's). Such exemplary set can be referred to as an "Ecosystem." The exemplary system, method, and computer-accessible medium can reduce or eliminate over-fitted models by using an empirical Bayes approach to control false-discovery rates in multiple hypotheses testing.
2. Exemplary Ranking: All models can be assumed to be generative; the generated data can be compared to future data in order to provide a rank function ("Rank (M, D)").
3. Exemplary Oracle(s): For example, a model M* can exist that on a data set D can perform exactly, without any error. Thus, there can be a distance function such that Distance(D(M*), D)=0 where D(M*) is the data generated by M*. Thus Rank(M *, D) can be superior to Rank(M, D) for any M in the ecosystem.
4. Exemplary Goal: Use a recommender-verifier system in a signaling game to identify the best approximation to oracle M* for a domain D.

The exemplary architecture can include generating an ecosystem of exemplary AI models. The exemplary models can be contributed to by a set of users called recommenders and can be verified before inclusion by another set of users called verifiers. Multiple AI modules ("Models" M's) can be provided in an ensemble working on multiple data sets ("Domains" D's). Such a set can be referred to as an "Ecosystem." The exemplary system, method, and computer-accessible medium, according to an exemplary embodiment of the present disclosure, can filter and or eliminate various over-fitted models using, for example, an empirical Bayes approach to control false-discovery rate in multiple hypotheses testing.

Exemplary Ranking: All models can be assumed to be generative; the generated data can be compared to future data in order to provide a rank function ("Rank(M, D)").

Exemplary Oracle: A model M* can be provided that on a data set D can perform exactly, without any error. An exemplary distance function can be included such that Distance(D(M *), D)=0, where D(M*) can be the data generated by M*. Thus, Rank(M*,D) can be superior to Rank(M,D) for any M in the ecosystem.

Exemplary Goal: A recommender-verifier system in a signaling game can be used to identify the best approximation to oracle M* for a domain D.

FIG. 1 shows an exemplary diagram illustrating market competition according to an exemplary embodiment of the present disclosure. A set of agents can be assumed to participate in the game to rank a model M (e.g., either an existing one, combination of existing ones or a new one). They can be referred to as Recommenders 105 and Verifiers 110.

Recommenders 105 agent can select a domain and a data-set D 115 associated with the domain and a model M, which can include various financial data 120. Recommender 105 can publish hypotheses in support of M (e.g., why (M,D) may best approximate M*, for example, using qualitative reasoning, causal support, past history, or new computational analysis on real or synthetic data). Recommender 105 can stake some utilities (e.g. tokens). The utilities can include, but are not limited to, the Recommender's reputation or a financial stake (e.g., hard currency, digital currency, cryptocurrency, etc.). If the recommended model does not lead to a competition, Recommender 105 can lose the stake. Recommender 105 can also publish an estimated rank RankR(M,D).

In order to analyze a model provided by Recommender 105, the exemplary system, method, and computer-accessible medium can determine whether or not there is at least one verifier associated with the model. Verifiers 110 can select one or more models provided by Recommenders 105, and can rank each of the models. If no verifier 110 chooses to verify and/or rank a model, then the exemplary system, method, and computer-accessible medium may not analyze the specific model, and the model can be removed or discarded. Each verifier 110 can also provide a stake when verifying the models. The stake can include a financial stake (e.g., hard currency, digital currency, cryptocurrency, etc.). One or many Verifiers 110 can provide their estimated ranks of the model: RankV (M, D). If a verifier 110 does verify and/or rank a model, then the exemplary system, method, and computer-accessible medium can analyze the specific model depending on the number of verifiers that analyze and/or rank the model. Additionally, even if one verifier 110 verifies and/or ranks a model, the exemplary system, method, and computer-accessible medium may still not analyze the model depending on the stake put forth.

For example, if only a single verifier chooses a specific model, then the exemplary system, method, and computer-accessible medium may not analyze the model based on only a single verification. Additionally, if multiple verifiers choose a model, but each verifier only puts a small stake on the model, then the exemplary system, method, and computer-accessible medium also may not analyze this model. Thus, the exemplary system, method, and computer-accessible medium can utilize a specific set of criteria that is based on the number of verifiers choosing specific models, and the total amount of the stake put on the specific model. An exemplary weight can be generated and/or determined based on the number of verifiers and the amount of stake. If the determined weight is below a particular threshold, then the exemplary system, method, and computer-accessible medium may not analyze the specific model. If the weight is above a particular threshold, then the exemplary system, method, and computer-accessible medium can analyze the specific model.

The exemplary system, method, and computer-accessible medium, according to an exemplary embodiment of the present disclosure, can perform an exemplary test to determine if the true rank Rank(M, D) is above or below the median of the ranks estimated by Verifiers 110. If the rank is above the median, then half of the Verifiers 110 who estimated a rank above the median win, and the other half of the Verifiers 110 who estimated a rank below the median lose. All models found eligible (e.g., eligible models 125) for competition can be included in the eco-system, together with its computed rank (or its recommended rank, if no verifier challenges it). Ineligible models 130 can be excluded. Losers can provide some utilities (e.g., tokens) to the winners. For example, the utilities collected from the Recommenders 105 and Verifiers 110 can be pooled together. The winners (e.g., the verifiers who correctly verified the models), can be provided a portion of the pooled utilities. However, the losers do not receive any of the pooled utilities, and they also forfeit their own stake. The pool can be divided based on the amount of stake put in by one verifier compared to other verifiers.

For example, Recommender 105 can develop a strong Oracle-like model. He/She can then be incentivized to contribute the model to the ecosystem as he/she can be sure that it can attract sufficiently many Verifiers 110 (e.g., resulting in no loss of stake); he/she can also expect a win from Verifiers 110 who will underestimate the power of the model. (Note: Recommender 105 may also play the role of Verifier 110 for a difference recommender). Additionally, over time, weak recommenders whose models do not lead to competitions can be pruned out. Independent of the result of the competition, an Oracle-like model can be evaluated, and can be included in the eco-system (e.g., if and only if it is eligible for competition). There may be further opportunities to earn rent from the future use of the model in the ecosystem.

A "good" (or acceptable) recommender can avoid contributing weak random variations of an oracle model once it has been achieved, while the domain is stationary. In this case, most strong verifiers can bet against him and win. A recommender can also be incentivized to work on a domain where the models can be further improved (e.g., instead of investing in a domain that already has an Oracle-model or a strong approximation to it.) This situation can also arise as a result of the non-stationarity of data. A weak recommender can be deterred by the fact that his/her recommendations may not be eligible for competition, and can result in loss of stake. In addition, just introducing black boxes without any reasoning, or domain-specific prior, can attract strong verifiers who can bet against him. Similarly, a weak verifier may not be able to accumulate utilities as he/she can accumulate more losses than wins (e.g., assuming that there are other informed verifiers). Thus, the exemplary system, method, and computer-accessible medium can provide (i) liveness via Recommenders who can be incentivized to introduce new models to the system as well as (ii) safety via Verifiers who can ensure that non-competitive, or non-verified, models can accumulate in the system.

Exemplary Building Utilities

The exemplary system, method, and computer-accessible medium, according to an exemplary embodiment of the present disclosure, can also utilize costly signaling in accordance with principles of financial engineering. For this purpose, the existence of a cryptographic security token system that distributes tokens to Recommenders and Verifiers in exchange of financial investments can be assumed. These tokens can be used in the dynamics of the exemplary game. In addition, there can be rent to be collected by allowing other agents (e.g., senders and receivers) to use the models in the ecosystem for other applications, where AI can be used productively. The rent for the models can be calculated by classical financial engineering approaches (e.g., CAPM, Capital Asset Pricing Models).

Exemplary FinTech Competitions

The exemplary system, method, and computer-accessible medium can analyze FinTech, though the similar structures can be used for other domains mutatis mutandis. Modern Fintech can build on a wide range of disciplines (e.g., from computer and data sciences, at one end of the spectrum, to finance, artificial intelligence, game theory and mathematics at the other). It can be focused on a central aspect of modern economic life (e.g., finance, a multi-faceted subject that draws on ideas from mathematics, economics, psychology and other social and political sciences, and increasingly, information technology and how it connects to society and social networks). In the last half of the century, with expanding data sources and increasing computing speed, finance has become more reliant on statistics, data, and econometric models, slowly paving the way to newer forms of financial engineering and technologies as well as their management and regulation—often by computational means.

"FinTech" can refer to financial sector innovations involving technology-enabled economic models that can eliminate market inefficiency, support synchronicity in the market and can improve risks and liquidity, facilitate disintermediation, revolutionize how existing and emerging firms create and deliver products and services, address privacy, trust and personalization, regulatory and law-enforcement challenges, and seed opportunities for inclusive growth. Some of these innovations can substantially improve the economic life of a larger number of citizens, but may need the development of new approaches to understand their opportunities and challenges.

The evolving applications of FinTech has encountered a methodological problem, common to many domains using Data Science and Artificial Intelligence. Specifically, (i) how does one quantitatively measure how much better an AI-based FinTech system performs in comparison to traditional approaches from statistical inference, econometrics, model-based (Bayesian) analysis, etc., (ii) how does one disentangle the improvements attributable to model selection, data size, special purpose computation (e.g., GPU), etc.?, and (iii) how does one decide how to design future systems for a suitable application (e.g., ones with information asymmetry and illiquidity), a suitable computational infrastructure (e.g., clouds with special purpose software like Map-reduce or BigQuery) and a suitable data sets (e.g., social media data vs. cancer genomics data)?

The exemplary system, method, and computer-accessible medium can utilize empirical analysis. This can include maintaining an eco-system of models, with additional information such as how the model was introduced, what information was provided, a preliminary empirical Bayesian evaluation of its goodness (e.g., rank), competition involving additional verifiers and the results. For succinctness, an aggregated rank for each model in the eco-system (e.g., specific to a particular domain) can be displayed.

The exemplary system, method, and computer-accessible medium can be used to evaluate data science, machine learning, and AI based FinTech systems, to be used by the applied finance community. Statistical arbitrage, pricing models with metrics for risks and liquidity and the changes in the underlying market and regulatory microstructures, can be determined using the exemplary system, method, and computer-accessible medium. The exemplary system, method, and computer-accessible medium can be used to gather real-time information about various FinTech and RegTech technologies in an international setting (e.g., US, India and China), and can be used to setup the technology evaluation on a broader dataset. Its users can set up a base for economic, financial, mathematical and computational scientists to work together and solve complex fundamental problems in economics, computing, intelligence and learning.

Exemplary Rationale: Currently most powerful AI approaches are based on supervised learning. They are fairly simple in the formulation of the problems, but have performed surprisingly well in tasks that are mostly attributed to complex human skills (e.g., handwriting recognition, spam detection, image recognition, tagging humans in images, creating captions for images, language translation, etc.). It has been argued that such approaches, can only capture roughly one second of human cognition; roughly the tasks that can be performed by a large group of Mechanical Turks, engaged in labeling raw data.

For example, in the classical context, AI, and more precisely, Machine Learning, can include two fundamental spaces. The first space D can include data points (e.g., point clouds in a high dimensional space) and the second space M can include learning models (e.g., parameters of a distributions or weights of a multi-layer artificial neural net, etc.). In statistical learning, M can be a space of statistical models $\{p(x, M): M \in \mathcal{M}\}$ in the generative case or $\{p(y|x; M): M \in \mathcal{M}\}$ in the discriminative case. The space M can be either a low dimensional parametric space or the space of all suitably sparse models in non-parametric space. While classical statistical estimation theory has focused on the former, there is a significant emphases on the later in machine learning—our primary focus here.

The exemplary system, method, and computer-accessible medium, according to an exemplary embodiment of the present disclosure, can utilize a machine learning algorithm to determine a model $M \in \mathcal{M}$ based on a training sample $\{(x_i, y_i)n/i=1 \subseteq x \times y\}$. The model determination can be formalized as an optimization problem in two parts: (i) guarding against underfitting by maximizing likelihood, margin, distance/divergence or utility, or minimizing a loss function, together with (ii) guarding against overfitting by regularizing with shrinkage, entropy, information or sparsity, or a proxy such as L norms, etc. There can be a lack of an all-encompassing theory to compare various model selection approaches used by machine learning software, even in a specific domain such as Fintech, and nonconclusive anecdotal arguments based on empirical studies on benchmark data sets have been poor substitute for a deeper understanding.

The exemplary system, method, and computer-accessible medium, according to an exemplary embodiment of the present disclosure, can facilitate the study a wide class of AI procedures developed specifically for Fintech. For example, the exemplary system, method, and computer-accessible medium can facilitate multiple hypothesis testing (e.g., each model $m_i \in \mathcal{M}$ ] learned from a training data set $D_T = \{(x_i, y_i)n/i=1 \subseteq x \times y$ can correspond to a hypothesis that it can perform with a specific "score" $s_i$ on an unseen cross validating data set $D_V = \{(x_i, y_i)m/i=1 \subseteq x \times y$. In particular, the prototype can use Efron's Empirical Bayes[1, 2, 3] approaches to control false discovery rates ("fdr") and measure how well models from each family of machine learning procedures is likely to win such a "horse race." This likelihood can be used to determine if a recommended model can be eligible for "competition," and thus included in the eco-system.

Various exemplary methods available in various AI open source platforms (e.g., WEKA, H2O, TensorFlow, OpenAI, Caffe, CNTK, Mahout, etc0 can be used. The exemplary system, method, and computer-accessible medium can utilize finance data, and can implement most of the commonly used models (e.g., regressions, classification trees, neural nets (DNN and ENN: respectively Deep and Evolutionary Neural Nets), etc.). The data source the prototype can use can be determined from proprietary financial data collected by a large bank. The multiple hypotheses testing procedures (e.g., discussed above), can be applied to models derived from training data spanning several years with the cross validation applied to the last year of data. The overall success of the entire framework can be tested by applying only the truly successful machine learning models to financial data arriving in real-time over six months subsequent to the end of full analysis.

The exemplary system, method, and computer-accessible medium, according to an exemplary embodiment of the present disclosure, can support an ecosystem of models that have already been tried. When a new model is recommended, the exemplary system, method, and computer-accessible medium can perform a preliminary analysis of the model being introduced and a competition can be deemed eligible if and only if the proposed model passes the analysis outlined here.

Many machine learning procedures currently in use suffer from several shortcomings that make them less than ideal for Fintech applications: (i) these procedures can assume a stationary distributions over x×y, and only capture an instantaneous response to the new incoming data; (ii) they can be "black boxes," and can be difficult to interpret or use in a strategic interventions; and (iii) they can be blind to "black swan events," costly adversarial events that can be rare, but are plausible. In order to remedy these disadvantages, machine learning procedures can be facilitated to understand the causal structures in the data and be amenable to stress testing that require causal generative models consistent with causal structures.

In order to address these issues, graphical models that can capture causal structures via a directed acyclic graphs ("DAG") can be analyzed, whose directed edges can correspond to Suppes' notions of prima-facie causes. These exemplary models (e.g., Suppes-Bayes Causal Nets ("SBCN")) can be regularized using Bayes Information Criterion ("BIC") to eliminate spurious prima-facie causes and only retain genuine causes, supported by the training data.

Suppes notion of probabilistic causation is based on two ideas: (a) temporal priority (e.g., causes precede effect) and (b) probability raising (e.g., causes raise the conditional probability of the effect in the presence of the causes relative to its absence); these two notions are easily captured in a logic, called probabilistic computational tree logic ("PCTL"), which can support efficient polynomial time model checking procedures.

Once an SBCN can be constructed over financial factors (e.g., Fama French Five Factor Models), it can be possible to traverse the graph to generate plausible adversarial rare trajectories that can stress test a particular discriminative model (e.g., as the ones described earlier). Using these stress testing procedures, the best AI models selected earlier can be analyzed to further identify robust profit-generating models. If the recommended model enters a competition, the recommender may publish the results of the causal analysis.

Figure 2:
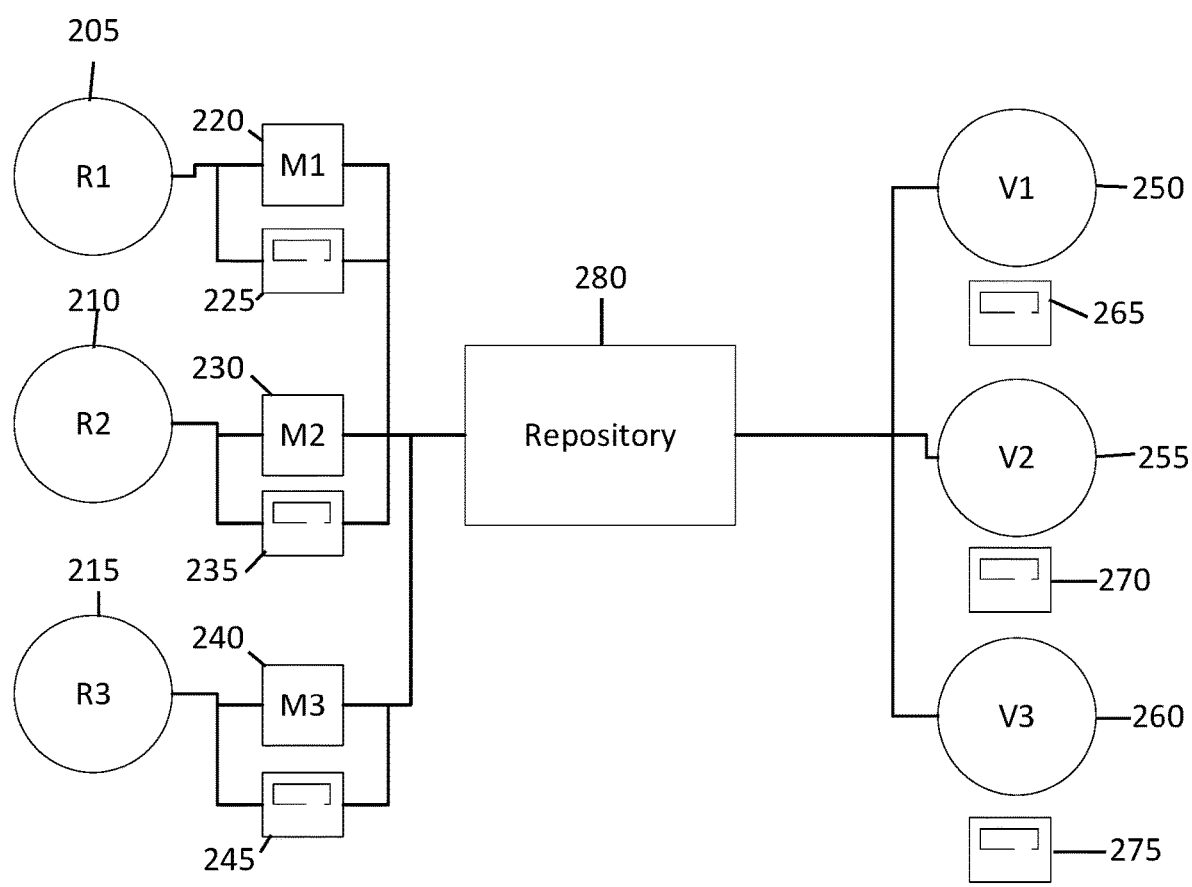
FIG. 2 is an exemplary diagram of a system for recommending a model according to an exemplary embodiment of the present disclosure.

FIG. 2 shows an exemplary diagram of a system for recommending a model according to an exemplary embodiment of the present disclosure. For example, multiple recommenders (e.g., Recommenders 205, 210, and 215), can generate or select their own models (e.g., models 220, 230, and 240) for review and verification. Each recommender 205, 210, and 215 can stake some form of currency or utility (e.g., utilities 225, 235, and 245). Each utility can be a physical currency, a digital currency, a cryptocurrency, or a reputation of the recommender. Each model 220, 230, and 240 can be submitted to repository 280 for review and verification. Multiple verifiers (e.g., verifiers 50, 255, and 260) can review and verify each model 220, 230, 240. Each verifier can stake their own currency or utility (e.g., utilities 265, 270, and 275). Models 220, 230, and 240 can be ranked by verifiers 250, 255, and 260, and based on the ranking, one or more of verifiers 250, 255, and 260 can be determined to have won or lost. Verifiers who win can receive some of the utility put up by recommenders 205, 210, 215, and verifiers 250, 255, and 260. Verifiers who have lost can lose their utility.

Exemplary Machine Learning

The exemplary system, method, and computer-accessible medium can utilize machine learning to review and verify the various exemplary models. Various datasets (e.g., financial datasets, medical datasets, etc.), can be analyzed and used to test and verify the models. The exemplary system, method, and computer-accessible medium can utilize various neural networks, such as convolutional neural networks ("CNN") or recurrent neural networks ("RNN") to generate the exemplary models. A CNN can include one or more convolutional layers (e.g., often with a subsampling step) and then followed by one or more fully connected layers as in a standard multilayer neural network. CNNs can utilize local connections, and can have tied weights followed by some form of pooling which can result in translation invariant features.

A RNN is a class of artificial neural network where connections between nodes form a directed graph along a sequence. This facilitates the determination of temporal dynamic behavior for a time sequence. Unlike feedforward neural networks, RNNs can use their internal state (e.g., memory) to process sequences of inputs. A RNN can generally refer to two broad classes of networks with a similar general structure, where one is finite impulse and the other is infinite impulse. Both classes of networks exhibit temporal dynamic behavior. A finite impulse recurrent network can be, or can include, a directed acyclic graph that can be unrolled and replaced with a strictly feedforward neural network, while an infinite impulse recurrent network can be, or can include, a directed cyclic graph that may not be unrolled. Both finite impulse and infinite impulse recurrent networks can have additional stored state, and the storage can be under the direct control of the neural network. The storage can also be replaced by another network or graph, which can incorporate time delays or can have feedback loops. Such controlled states can be referred to as gated state or gated memory, and can be part of long short-term memory networks ("LSTMs") and gated recurrent units RNNs can be similar to a network of neuron-like nodes organized into successive "layers," each node in a given layer being connected with a directed e.g., (one-way) connection to every other node in the next successive layer. Each node (e.g., neuron) can have a time-varying real-valued activation. Each connection (e.g., synapse) can have a modifiable real-valued weight. Nodes can either be (i) input nodes (e.g., receiving data from outside the network), (ii) output nodes (e.g., yielding results), or (iii) hidden nodes (e.g., that can modify the data en route from input to output). RNNs can accept an input vector x and give an output vector y. However, the output vectors are based not only by the input just provided in, but also on the entire history of inputs that have been provided in in the past.

Figure 3:
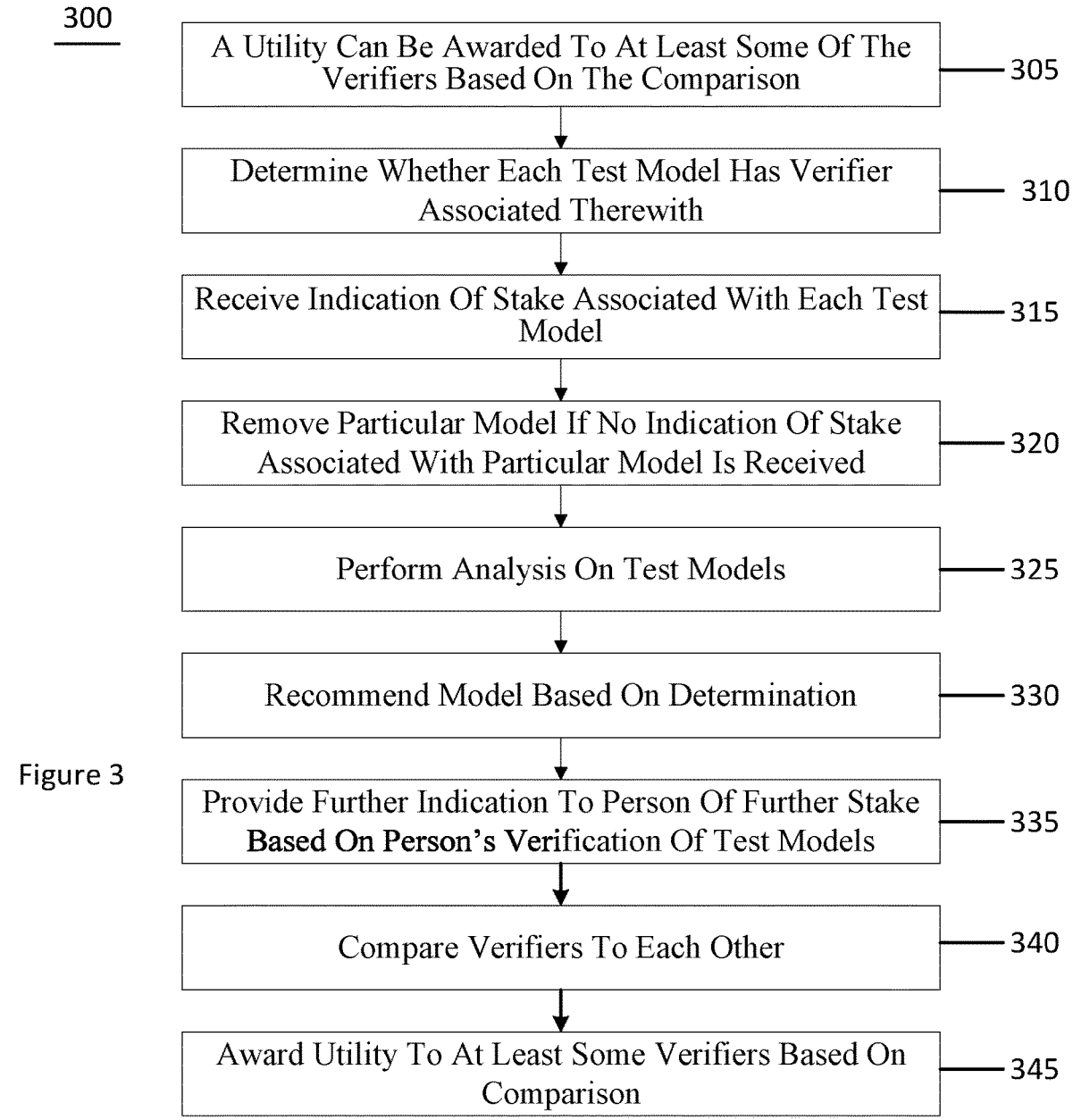
FIG. 3 is a flow diagram of an exemplary method for recommending a model according to an exemplary embodiment of the present disclosure.

FIG. 3 is a shows a flow diagram of an exemplary method 300 for recommending a model according to an exemplary embodiment of the present disclosure. For example, At procedure 305, a plurality of test models including the model can be received. At procedure 310, a determination can be made as to whether each of the test models has at least one verifier associated therewith. At procedure 315, an indication of a stake associated with each of the test models can be received. At procedure 320, a particular model can be removed if no indication of a stake associated with the particular model is received. At procedure 325, an analysis can be performed on at least one of the test models. At procedure 330, the model can be recommended based on the determination. At procedure 335, a further indication can be provided to the person of a further stake based on the person's verification of the test models. At procedure 340, each of the verifiers can be compared to each other. At procedure 345, a utility can be awarded to at least some of the verifiers based on the comparison.

Figure 4:
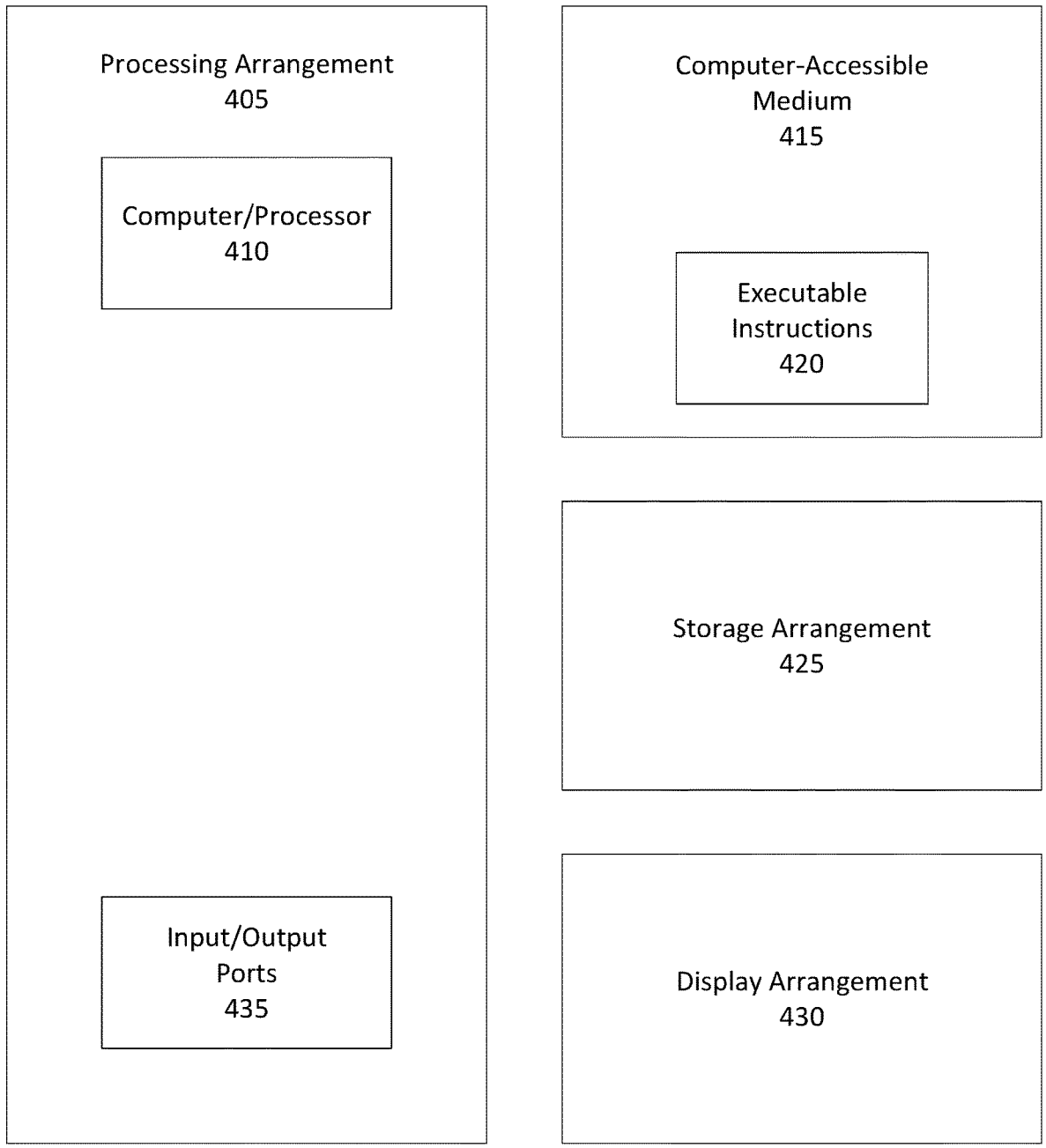
FIG. 4 is an illustration of an exemplary block diagram of an exemplary system in accordance with certain exemplary embodiments of the present disclosure.

FIG. 4 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 405. Such processing/computing arrangement 405 can be, for example entirely or a part of, or include, but not limited to, a computer/processor 410 that can include, for example one or more microprocessors, and use instructions stored on a computer-accessible medium (e.g., RAM, ROM, hard drive, or other storage device).

As shown in FIG. 4, for example a computer-accessible medium 415 (e.g., as described herein above, a storage device such as a hard disk, floppy disk, memory stick, CD-ROM, RAM, ROM, etc., or a collection thereof) can be provided (e.g., in communication with the processing arrangement 405). The computer-accessible medium 415 can contain executable instructions 420 thereon. In addition or alternatively, a storage arrangement 425 can be provided separately from the computer-accessible medium 415, which can provide the instructions to the processing arrangement 405 so as to configure the processing arrangement to execute certain exemplary procedures, processes, and methods, as described herein above, for example.

Further, the exemplary processing arrangement 405 can be provided with or include an input/output ports 435, which can include, for example a wired network, a wireless network, the internet, an intranet, a data collection probe, a sensor, etc. As shown in FIG. 4, the exemplary processing arrangement 405 can be in communication with an exemplary display arrangement 430, which, according to certain exemplary embodiments of the present disclosure, can be a touch-screen configured for inputting information to the processing arrangement in addition to outputting information from the processing arrangement, for example. Further, the exemplary display arrangement 430 and/or a storage arrangement 425 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, and drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference, in their entireties:
[1] B. Efron and T. Hastie, Computer Age Statistical Inference: Algorithms, Evidence and Data Science. Cambridge University Press, 2016.
[2] B. Efron, "Bayes, oracle bayes, and empirical bayes," 2017.
[3] S. Wager, T. Hastie, and B. Efron, "Confidence intervals for random forests: the jackknife and the infinitesimal jackknife," Journal of Machine Learning Research, vol. 15, no. 1, pp. 1625-1651, 2014.
[4] I. J. Goodfellow, Y. Bengio, and A. C. Courville, Deep Learning. Adaptive computation and machine learning, MIT Press, 2016.
[5] I. J. Goodfellow, "NIPS 2016 tutorial: Generative adversarial networks," CoRR, vol. abs/1701.00160, 2017.
[6] S. Kleinberg and B. Mishra, "The temporal logic of token causes," in Principles of Knowledge Representation and Reasoning: Proceedings of the Twelfth International Conference, K R 2010, Toronto, Ontario, Canada, May 9-13, 2010, 2010.
[7] S. Kleinberg and B. Mishra, "The temporal logic of causal structures," in UAI 2009, Proceedings of the Twenty-Fifth Conference on Uncertainty in Artificial Intelligence, Montreal, QC, Canada, Jun. 18-21, 2009, pp. 303-312, 2009.
[8] G. Gao, B. Mishra, and D. Ramazzotti, "Efficient simulation of financial stress testing scenarios with suppes-bayes causal networks," in International Conference on Computational Science, ICCS 2017, 12-14 Jun. 2017, Zurich, Switzerland, pp. 272-284, 2017.

What is claimed is:

1. A non-transitory computer-accessible medium having stored thereon computer-executable instructions for recommending at least one eligible artificial intelligence model, wherein, when a computing arrangement executes the instructions, the computing arrangement is configured to perform procedures comprising:
receiving a plurality of test models recommended by a plurality of computer recommending agents including the at least one eligible artificial intelligence model;
determining, with respect to each of the plurality of test models, whether one or more of a plurality of computer verifying agents selected the test model;
analyzing, via an artificial intelligence model, one or more of the plurality of test models that were selected by computer verifying agents;
training the artificial intelligence model on one or more cross validating training data sets, wherein the one or more cross validating training data sets train the artificial intelligence model to guard against (i) underfitting by one or more of maximizing a likelihood, a margin, a distance/divergence or a utility, and (ii) overfitting by regularizing with one or more of shrinkage, entropy, information or sparsity; and
recommending the at least one eligible model based on the selection of the eligible artificial intelligence model by the one or more of a plurality of computer verifying agents as well as the analysis of the eligible artificial intelligence model.

2. The non-transitory computer-accessible medium of claim 1, wherein the computer arrangement is further configured to receive an indication of a stake associated with each of the test models.

3. The non-transitory computer-accessible medium of claim 2, wherein the stake is at least one of a financial stake or a reputation stake.

4. The non-transitory computer-accessible medium of claim 1, wherein the computer arrangement is further configured to analyze at least one of the test models using a machine learning procedure.

5. The non-transitory computer-accessible medium of claim 4, wherein the machine learning procedure includes at least one of a convolutional neural network or a recurrent neural network.

6. The non-transitory computer-accessible medium of claim 1, wherein the computer arrangement is further configured to analyze at least one of the test models using empirical Bayes procedure.

7. The non-transitory computer-accessible medium of claim 1, wherein the computer arrangement is further configured to remove at least one particular model if the at least one particular model does not have at least one verifier associated therewith.

8. The non-transitory computer-accessible medium of claim 1, wherein the at least one verifier is at least one person testing at least some of the test models.

9. The non-transitory computer-accessible medium of claim 8, wherein the computer arrangement is configured to receive an indication of a stake from the at least one person associated with the verification of the test models.

10. The non-transitory computer-accessible medium of claim 9, wherein the stake is a financial stake.

11. The non-transitory computer-accessible medium of claim 10, wherein the financial stake is a cryptocurrency.

12. The non-transitory computer-accessible medium of claim 9, wherein the computer arrangement is configured to provide a further indication to the at least one person of a further stake based on the at least one person's verification of the test models.

13. The non-transitory computer-accessible medium of claim 1, wherein the at least one verifier is configured to rank each of the test models.

14. The non-transitory computer-accessible medium of claim 1, wherein the computer arrangement is further configured to analyze at least one of the test models using at least one dataset.

15. The non-transitory computer-accessible medium of claim 14, wherein the at least one dataset is a financial dataset or a medical dataset.

16. The non-transitory computer-accessible medium of claim 1, wherein the at least one verifier includes a plurality of verifiers, and wherein the computer arrangement is further configured compare each of the verifiers to each other.

17. The non-transitory computer-accessible medium of claim 16, wherein the computer arrangement is further configured to award a utility to at least some of the verifiers based on the comparison.

18. The computer-accessible medium of claim 1, wherein the artificial intelligence model is further trained to control for false discovery rates.

19. A system for recommending at least one eligible artificial intelligence model, comprising:
a computer hardware arrangement comprising at least one processor, configured to:
receive a plurality of test models recommended by a plurality of computer recommending agents including the at least one eligible artificial intelligence model;
determine, with respect to each of the plurality of test models, whether one or more of a plurality of computer verifying agents selected the test model;
analyze, via an artificial intelligence model, one or more of the plurality of test models that were selected by computer verifying agents;
train the artificial intelligence model on one or more cross validating training data sets, wherein the one or more cross validating training data sets train the artificial intelligence model to guard against (i) underfitting by one or more of maximizing a likelihood, a margin, a distance/divergence or a utility, and (ii) overfitting by regularizing with one or more of shrinkage, entropy, information or sparsity; and
recommend the at least one eligible neural network model based on the selection of the eligible artificial intelligence model by the one or more of a plurality of computer verifying agents as well as the analysis of the eligible artificial intelligence model.

20. A method for recommending at least one eligible artificial intelligence model, comprising:
receiving a plurality of test models recommended by a plurality of computer recommending agents including the at least one eligible artificial intelligence model;
determining, with respect to each of the plurality of test models, whether one or more of a plurality of computer verifying agents selected the test model;
analyzing, via an artificial intelligence model, one or more of the plurality of test models that were selected by computer verifying agents;
training the artificial intelligence model on one or more cross validating training data sets, wherein the one or more cross validating training data sets train the artificial intelligence model to guard against (i) underfitting by one or more of maximizing a likelihood, a margin, a distance/divergence or a utility, and (ii) overfitting by regularizing with one or more of shrinkage, entropy, information or sparsity; and
using a computer hardware arrangement, recommending the at least one eligible artificial intelligence model based on the selection of the eligible model by the one or more of a plurality of computer verifying agents as well as the analysis of the eligible artificial intelligence model.

* * * * *